United States Patent
Fahy

(10) Patent No.: US 7,250,292 B2
(45) Date of Patent: Jul. 31, 2007

(54) HYPERTONIC REDUCTION OF CHILLING INJURY

(75) Inventor: Gregory M. Fahy, Corona, CA (US)

(73) Assignee: 21st Century Medicine, Rancho Cucamonga, CA (US)

( * ) Notice: Subject to any disclaimer, the term of this patent is extended or adjusted under 35 U.S.C. 154(b) by 83 days.

(21) Appl. No.: 09/916,032

(22) Filed: Jul. 26, 2001

(65) Prior Publication Data

US 2002/0042042 A1    Apr. 11, 2002

Related U.S. Application Data

(63) Continuation-in-part of application No. 09/771,221, filed on Jan. 26, 2001, now abandoned.

(60) Provisional application No. 60/178,157, filed on Jan. 26, 2000.

(51) Int. Cl.
*C12N 5/00* (2006.01)
*C12N 5/02* (2006.01)

(52) U.S. Cl. ..................... 435/325; 435/404
(58) Field of Classification Search ............. 435/243, 435/325, 374, 260, 404
See application file for complete search history.

(56) References Cited

U.S. PATENT DOCUMENTS 5,328,821 A * 7/1994 Fisher et al. ............ 435/1.3
5,693,534 A * 12/1997 Alak et al. .............. 435/366
5,723,282 A * 3/1998 Fahy ...................... 435/1.3
6,274,303 B1 * 8/2001 Wowk et al. ............ 435/1.3
6,395,467 B1 * 5/2002 Fahy et al. .............. 435/1.3
6,492,103 B1 * 12/2002 Taylor .................... 435/1.2
6,616,858 B2 * 9/2003 Fahy et al. .............. 252/70

FOREIGN PATENT DOCUMENTS

WO    WO 97/45010    12/1997

\* cited by examiner

*Primary Examiner*—David M. Naff
*Assistant Examiner*—Deborah K. Ware
(74) *Attorney, Agent, or Firm*—Foley & Lardner LLP; Stephen E. Reiter

(57) ABSTRACT

This invention relates generally to cryopreservation and a method for preventing injury caused by cooling and warming of tissue and for reducing the toxicity of vitrification solutions. The present method achieves reduction or elimination of injury by increasing the tonicity of the medium to greater than isotonic prior to cooling. The method was developed by attempting to simulate without freezing, the events that take place during freezing living cells and/or tissue. A further benefit of the method is that, since the cryopreservation medium is hypertonic, it can be diluted to a more extreme degree in one step once the system is rewarmed, without engendering the degree of cell swelling that would attend the same dilution factor when diluting an isotonic cryopreservation medium.

21 Claims, 5 Drawing Sheets ured. Adding and removing the cryoprotectant can also induce damage, particularly if the addition and washout process is prolonged but also if dilution is too rapid. It would be desirable in the art to provide a method that allows a) rapid addition of cryoprotectant, b) rapid or slow cooling without cold shock or chilling injury, and c) rapid dilution of the cryoprotectant without osmotic shock after rewarming of the living system.
HYPERTONIC REDUCTION OF CHILLING INJURY

RELATED APPLICATIONS

This application is a Continuation in Part of U.S. patent application Ser. No. 09/771,221, filed Jan. 26, 2001, now abandoned, which claims priority to U.S. Provisional Application No. 60/178,157, filed Jan. 26, 2000.

FIELD OF THE INVENTION

This invention relates generally to the field of cryopreservation. More specifically, the present invention relates to a method for preventing injury caused by cooling and warming of tissue and for reducing the toxicity of vitrification solutions by reducing the amount of cryoprotectant needed to vitrify and for facilitating the rapid introduction and washout of cryoprotectant without toxicity or osmotic injury.

BACKGROUND OF THE INVENTION

During the cooling and warming of tissues or cells in cryoprotective solutions, the cells and tissues are often injured. Adding and removing the cryoprotectant can also induce damage, particularly if the addition and washout process is prolonged but also if dilution is too rapid. It would be desirable in the art to provide a method that allows a) rapid addition of cryoprotectant, b) rapid or slow cooling without cold shock or chilling injury, and c) rapid dilution of the cryoprotectant without osmotic shock after rewarming of the living system.

There are many ways for living systems to be injured by cooling to subzero temperatures and subsequently warming from subzero temperatures. If the system is frozen, it may be damaged mechanically from intracellular or extracellular ice, or by consequences of changes in the composition of the unfrozen portion of the semi-frozen environment. If the system is vitrified, these sources of injury may disappear, but other forms of injury are possible.

"Thermal shock" (also sometimes called cold shock) is injury caused by rapid cooling per se, and is reduced by reducing the cooling rate. Thermal shock injury has been stated to exist (see Fahy et al., in Cell Biology of Trauma, J. J. Lemasters and C. Oliver, Eds, CRC Press, 1995, pp. 333-356) within a narrow temperature window between 0° C. and about −20° C. in rabbit renal cortex, but not below, but is currently believed not to be a major issue, even though rapid cooling rates are desirable for vitrification to reduce the likelihood of ice formation and cryoprotectant toxicity.

Another possible source of injury is "chilling injury," which is a poorly-understood form of damage caused by exposure to low temperatures per se. Chilling injury is, for practical purposes, essentially not cooling rate dependent (except for small systems, which may escape from chilling injury at very rapid cooling rates), but instead is dependent primarily on the absolute temperature to which the system is cooled. Stated in another way, thermal shock is caused by rapid cooling and is reduced or eliminated by slow cooling, and chilling injury is caused by slow cooling and is not eliminated by rapid cooling, except perhaps possibly at very high cooling rates.

Another form of injury pertinent to vitrification (cryopreservation without ice formation on cooling) is devitrification. As the temperature in a vitrifiable system is brought close to the glass transition temperature, nucleation can generally occur. When the system is warmed up, nuclei formed in the vicinity of the glass transition temperature (Tg), which are unable to grow while the system remains below Tg, can grow and produce injury both intracellularly and extracellularly.

Another way of referring to injury that takes place upon cooling per se and that is not formally characterized as representing either thermal shock or chilling injury is to simply term such injury as being "cooling injury."

The primary barriers to cryopreservation by vitrification are cryoprotectant toxicity, chilling injury, and devitrification. Cryoprotectant toxicity has been greatly reduced by recent inventions involving the use of weak glass-forming agents and qv* analysis and is no longer a major limiting factor for cellular systems. Because devitrification can be reduced using low-toxicity cryoprotectants, ice blockers, and rapid warming, it is also currently of diminishing concern. Chilling injury, however, remains a substantial and largely intractable problem which is difficult to address in part because of its unknown origin. Although there have been studies on the biochemistry of chilling injury in natural systems, nothing is known about the sources of chilling injury in cells that do not suffer from chilling injury at 0° C. and that have been loaded with vitrifiable concentrations of cryoprotectants and cooled to subzero temperatures. Therefore, it would be particularly valuable to be able to circumvent cooling injury in order to improve the results of vitrification.

One patented method is known in the art for dealing with chilling injury in such systems (see U.S. Pat. Nos. 5,962,214 and 5,723,282). Fahy showed that kidneys or kidney slices exposed to high but sub-vitrifiable concentrations of cryoprotectant at 0° C. were severely damaged by cooling to −20 to −30° C. He found that by using lower concentrations of permeating cryoprotectants prior to cooling, the sensitivity to chilling injury could be eliminated at these temperatures. Additional cryoprotectant could then be introduced by diffusion or by perfusion at −20 to −25° C., with reduced or eliminated toxicity (see also Fahy et al., in Cell Biology of Trauma, J. J. Lemasters and C. Oliver, Eds, CRC Press, 1995, pp. 333-356, but especially FIG. 8, pg. 353, and discussion thereof; and Khirabadi et al., Cryobiology 31: 597, 1994, and Cryobiology 32: 543-544, 1995.)

Surprisingly, this prior art method was later found to have a fatal flaw: when tissues protected at about −25° C. using the method were subsequently cooled to Tg, they actually suffered dramatically more severe injury than if they had been cooled directly from 0° C. (Khirabadi et al., Cryobiology 37: 447, 1998). Lack of permeation of the extra cryoprotectant at −25° C. was ruled out as a cause of the cooling injury, since doubling the equilibration time at −25° C. had minimal if any effect on cooling injury although it greatly exacerbated toxic injury at −25° C. Therefore, whatever its virtues may have been, this prior art method is untenable.

Fahy et al. explained the basis of their prior art method as follows (see the Cell Biology of Trauma reference above, pp. 351-352). "Human erythrocytes do not normally experience cold shock when cooled to 0° C., but are rendered susceptible to cold shock by exposure to hypertonic solutions prior to cooling . . . If the same hypertonicity is introduced at a temperature below 10° C., the cells remain uninjured either at the temperature of exposure or upon subsequent cooling. The method for avoiding cold shock, then, is to cool through the critical temperature range in the presence of low concentrations [low tonicity] and to increase concentration [tonicity] only after this critical temperature interval has been safely traversed."

"In the case of the rabbit kidney, we were aware that osmotic shrinkage of tubular cells is induced by exposure to VS4 and V52, and that cell shrinkage appears to be required for cold shock injury in red cells. Since kidneys cooled to −30° C. in VS4 supported life about 60% of the time and kidneys cooled to −30° C. in V52 supported life 0% of the time, it seemed that a concentration not much below the 49% w/v concentration of VS4 should avoid cold shock entirely."

In discussing the results of an experiment designed to test the analogy between thermal shock injury in red blood cells and cooling injury in rabbit kidney slices, Fahy et al. conclude (from the same reference): "It thus appears that the analogy between cooling injury in rabbit kidney tissue and cold shock in human erythrocytes is valid."

Thus, it is clear that although much attention has been given to the problem of obviating cooling injury in the past, a method for preventing such injury is still needed.

SUMMARY OF THE INVENTION

There are methods in the prior art that involve the use of polymers or other impermeants to facilitate vitrification. In these methods, polymers are used to enhance vitrification tendency in place of extra penetrating cryoprotectant. However, in none of these methods is the polymer used for the purpose of inhibiting cooling injury (as opposed to injury caused by ice formation, which, by the definitions herein, does not constitute cooling injury). Because of this, no prior art method has achieved optimum cryopreservation, because, as disclosed herein, inclusion of too much polymer can negate protection from cooling injury, or even cause extra cooling injury compared to use of no polymer, while use of too little impermeant may fail to attain maximum protection, and there has been no awareness that cooling injury is modified by changes in polymer concentration, so cooling injury has varied at random with unguided changes in experimental conditions. Therefore, the current invention allows optimum cryopreservation to be achieved by optimizing the level of hypertonicity and the method for introducing and removing hypertonicity so as to optimize the negation of cooling injury, an opportunity not previously possible. In addition, no past method has used polymer, other impermeants, or carrier solution concentration changes to attain benefits by simulating freezing and thawing.

Therefore, one embodiment of the invention is a method for cooling living cells in vitrifiable media without engendering damage from cooling per se. Surprisingly, the method achieves the near-elimination of chilling or cooling injury using an approach that is opposite to the prior methods. The present method achieves reduction or elimination of injury by increasing the tonicity of the medium to greater than isotonic prior to cooling.

A further embodiment is the use of hypertonic medium to reduce both cryoprotectant toxicity and chilling injury, wherein the hypertonic medium is added and removed in a manner that simulates the effects of both freezing and thawing. In a further embodiment the hypertonic medium prevents cooling injury at subzero temperatures.

A further embodiment is the use of a hypertonic medium to reduce the time required to remove cryoprotectant from living cells, wherein the accelerated washout of cryoprotectant is achieved by simulating thawing (simultaneous dilution of the hypertonic medium and the cryoprotectant).

A further embodiment is the use of a hypertonic medium to protect living cells from dilution shock, wherein the protection is achieved by the presence of the hypertonic medium prior to dilution and maintained by simultaneous dilution of the cryoprotectant and the medium in at least roughly similar proportions.

In a further embodiment the method provides two stages of treatment with hypertonic media, in which the first stage tonicity and the second stage tonicity may differ, but in which the tonicity at both stages exceeds isotonic.

DETAILED DESCRIPTION OF THE PREFERRED EMBODIMENT

Figure 1:
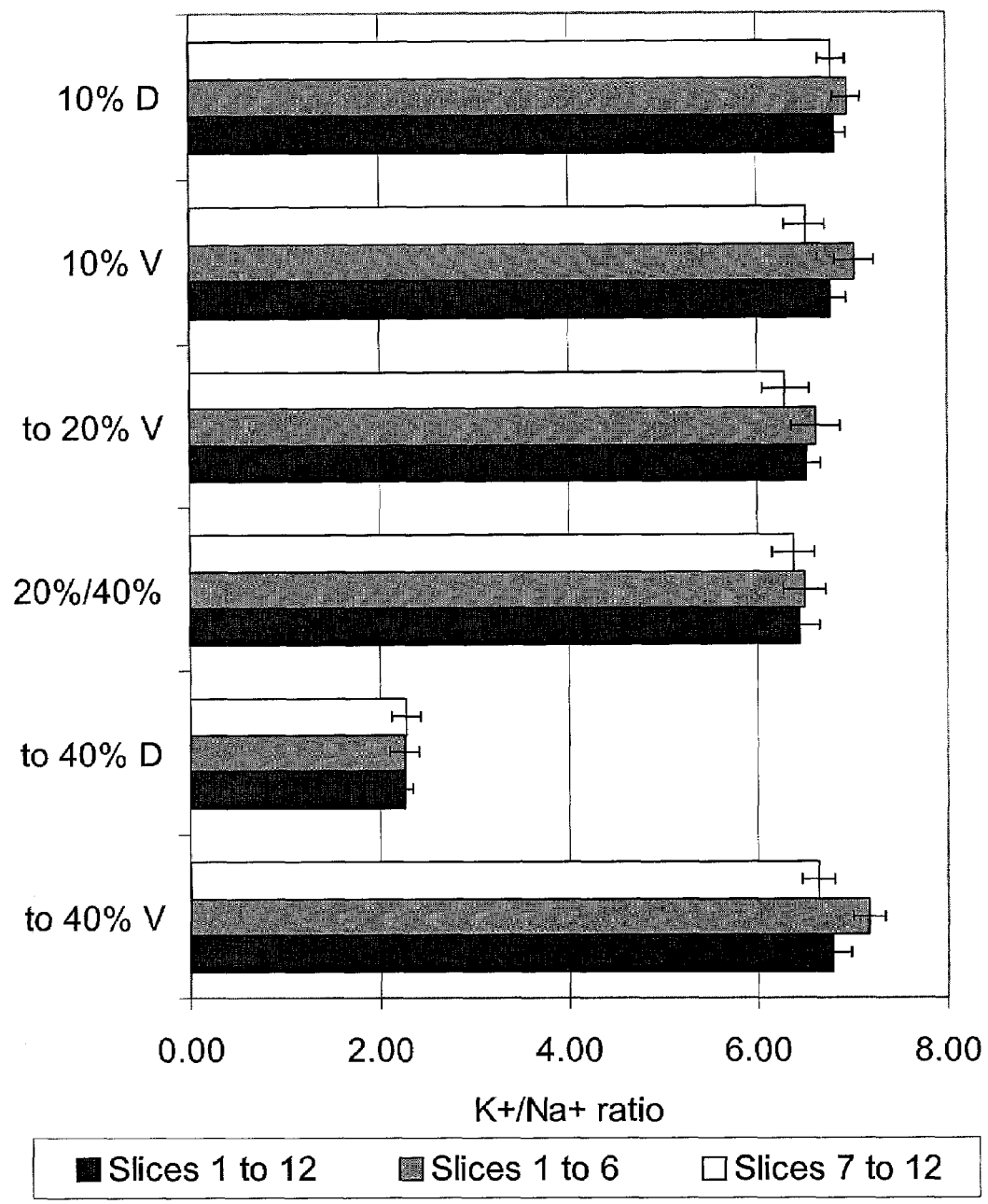
FIG. 1 shows the viability of frozen rabbit renal cortical slices subjected to simulated freezing in either DMSO (D) or Veg (V) at various concentrations. Viability is measured by tissue K/Na ratios after restoration of active metabolism. Each bar represents 6-12 individual slices.

An initial method for adding and removing cryopreservative with greater speed and greater safety and convenience approximately simulates, without freezing, the events that take place during the freezing and thawing of living cells and/or tissue is presented. This method uses hypertonicity of the medium and a return to medium isotonicity to add and remove cryoprotectants. As a result, the concentration of the cryoprotectants required for vitrification may be reduced, and/or the total exposure time required to adequately treat the system with cryoprotectants may be reduced, thereby reducing the toxicity of the vitrification solution.

This method has been broadened to achieve elimination of cooling injury at subzero temperatures in non-freezing cryoprotectant solutions by increasing the tonicity of the medium prior to cooling, with or without increasing the concentration of the vehicle solution constituents. Prior art methods involved decreasing the cryoprotectant concentration, and thus the transiently effective tonicity of the medium, prior to cooling. This protected against injury at higher temperatures (above −30° C.), but exacerbated injury at lower temperatures (below −30° C.). However, it is shown herein that, surprisingly, by increasing the tonicity, the cells are protected at both higher and lower subzero temperatures, without the need to reduce the cryoprotectant concentration to reduce cooling injury.

Definitions of Tonicity and the Effects of Solutes on Tonicity

The term "tonicity" refers to an observed effect of solutes on the volume of a cell exposed to a solution containing the solutes. Solutions may be permanently or transiently hypotonic, isotonic, or hypertonic depending upon their concentration and on the ability of the solutes in the solution to cross the cell membrane and enter and leave the cell.

If the volume of the cell in its natural state is not changed by transferring the cell into a solution, the solution is said to be observably "isotonic." This means that the solution has the same tonicity, or effective osmotic concentration, as the intracellular solution.

If the volume of the cell increases upon transfer to the solution, the solution is said to be "hypotonic." This means its effective osmotic concentration is below that of the intracellular solution.

If the volume of the cell decreases upon transfer to the solution, the solution is said to be "hypertonic," or effectively more osmotically concentrated than the intracellular solution.

If the solutes in the solution fail to permeate the cell, and if, during the time course of the observation, intracellular solutes do not leak out of the cell, then the tonicity of the solution depends only on the total osmotic concentration of the solution. In the body, extracellular solutes are rendered effectively impermeable by the sodium-potassium-ATPase "pump", and the osmotic concentration of extracellular fluids is about 285 mOsm (285 milliosmolal), as measured by freezing point depression {melting point equivalent to 0.285 osmolal×(−1.86° C./osmolal)=−0.53° C.} Therefore, an isotonic solution is one that has an effective osmolality of about 285 mOsm, although 300 mOsm can often be taken as an adequate approximation. A hypertonic solution will have an effective concentration greater than about 285-300 mOsm, and a hypotonic solution will have an effective concentration less than about 285-300 mOsm.

If a cell is placed into a 300 mOsm solution of dimethyl sulfoxide, a permeating solute, it will begin to swell. Because permeating solutes can enter the cell and exert an equal osmotic effect on both sides of the cell membrane, such solutes have no net effect on cell volume, once they have reached equilibrium. Therefore, they are effectively absent. Therefore, placing a cell into a 300 mOsm solution of dimethyl sulfoxide is similar to the effect of placing a cell into pure water. Because cell volume depends on osmosis, which is the movement of water from a high water concentration to regions of lower water concentration, a cell placed in water will swell. However, dimethyl sulfoxide is less permeable to a cell than is water, and therefore, cells placed in dimethyl sulfoxide (DMSO) will swell more slowly than cells placed into pure water.

A cell placed into a 600 mOsm solution of DMSO will initially shrink, not swell, due to the fact that the cell membrane is more permeable to water than it is to DMSO. In the extreme case of very low but finite permeability to DMSO, the cell will lose half of its water upon contact with 600 mOsm DMSO in order to increase cell concentration to twice the initial concentration (300 milliosmoles/kg of water becomes 600 milliosmoles per kg of water if the number of kg of water is reduced by half due to exosmosis.) Afterwards, however, the permeation of DMSO will continue and cell volume will increase. When the cell reaches its isotonic volume, it will contain about 300 mOsm DMSO and 300 mOsm of intracellular solute, balancing the osmotic pressure of the extracellular 600 mOsm solution. When the cell volume doubles, it will contain 150 mOsm of intracellular solute and 450 mOsm of DMSO. Swelling will tend to continue until the intracellular solute concentration is reduced to zero, which can only happen when cell volume reaches infinity. The point is that permeating solutes such as DMSO can be transiently hypertonic in the short run, even though they are the osmotic equivalent of water (hypotonic) once time has been allowed for permeation.

If a cell is placed into a solution containing 300 mOsm DMSO and 300 mOsm impermeable solute, the initial shrinkage of the cell will be the same as in the case of transferring the cell to 600 mOsm of DMSO in water, because the extracellular osmolality is the same in both cases. However, when the cell returns to isotonic volume, it will contain 300 mOsm DMSO and 300 mOsm intracellular solute, which will balance the 300 mOsm DMSO and 300 mOsm extracellular impermeant solute osmotically, and no further changes in cell volume will take place. This example illustrates the need for a "carrier solution" or "vehicle solution" for use in adding and removing permeable cryoprotectants. The carrier solution "carries" or delivers the cryoprotectant to the cell such that the cell will remain at its isotonic volume after the cryoprotectant has fully penetrated.

The tonicity of the carrier solution will determine the volume of the cell in the presence of cryoprotectant in the same way as impermeants control the volume of the cell in the absence of cryoprotectant, once cryoprotectant fluxes have ceased. As Meryman demonstrated (Cryobiology 19: 565-569, 1982), a normal tonicity is established in the presence of cryoprotectants by using impermeants at the same grams per unit solution volume (% w/v) or moles per unit solution volume (molarity) concentration units as would be appropriate in the absence of the cryoprotectant. This is logical because it is the cell volume one wishes to control, and establishing a given level of osmoles per unit volume outside the cell will result in the same level of osmoles per unit volume inside the cell, assuming the permeating cryoprotectants fully permeate and occupy the same volume fraction in the solution both intracellularly and extracellularly, a generally valid assumption.

Based on these definitions, the teachings of the prior art can now be translated as they relate to the prevention of cooling injury in highly cryoprotected systems (systems containing vitrifiable or near-vitrifiable concentrations of cryoprotectant).

Red blood cells placed into strongly hypertonic media (at least about 4 to 5 times more concentrated than normal, designated as 4-5X) at room temperature and cooled to 0° C. lyse when they reach about 10° C. However, if they are exposed to 4-5X solutions at 0° C. after prior cooling to 0° C. in an isotonic (1X) solution, they do not lyse. Furthermore, if red cells are exposed to 4-5X solutions at 0° C. and then cooled to subzero temperatures without freezing, they also do not lyse. So thermal shock in red cells is a specific event that takes place at 10° C. and only when the tonicity of the solution is high. High tonicity causes thermal shock injury, but only at higher temperatures. So if one wants to cool red cells to low temperatures in high-tonicity solutions, one must first cool them in low tonicity solutions to avoid thermal shock.

The prior art method for cryoprotected systems teaches that the transient hypertonicity experienced by cells placed into concentrated cryoprotectants sensitizes them to cooling injury in the same way hypertonic solutions are permissive of thermal shock in red cells. Therefore, reducing the cryoprotectant concentration, and thus the effective transiently hypertonic concentration of the cryoprotectant solution, prior to cooling below 0° C. eliminates cooling injury.

In the present disclosure, it is surprisingly found that a completely different strategy is both feasible and more effective than the prior art method.

EXAMPLES

In direct contradiction to the prior art method, the present method achieves elimination of cooling injury as well as other goals by increasing, not decreasing, the tonicity of the medium prior to cooling. There are two variants of the method. In the first variant, the medium is made hypertonic by increasing the concentration of the vehicle solution simultaneously with an increase in the concentration of the cryoprotectant(s). In the second variant, the medium is made hypertonic by adding non-toxic impermeant solute(s), and the non-toxic impermeant solute(s) need not be added at the same time as the permeating cryoprotectant(s) (the term "cryoprotectant" as used herein can refer to both a single cryoprotectant and a mixture of different cryoprotectants). In both variants of the hypertonic protection method, permeating cryoprotectant requirements may be reduced, exposure time to permeating cryoprotectants may be reduced, and faster and safer dilution of the cryoprotectants after use may be achieved, as well as protection from cooling-induced injury. Various combinations of the two primary variants of the hypertonic protection method are possible as well.

Adding impermeant solutes to cryoprotectants prior to cooling, blocks cooling injury without the need to reduce the concentration of cryoprotectants to preclude cooling injury. Furthermore, two thermal regimes are recognized herein for hypertonic reduction of cooling injury, and include means for optimizing the reduction of cooling injury by using optimized hypertonic protection over both thermal regimes. The first variant of these methods is a method in which the carrier solution for cryoprotectants can be made more concentrated in order to both reduce the concentration of permeating agents needed for vitrification and to facilitate rapid washout of the cryoprotectants, in analogy to the processes of freeze-concentration and thawing-mediated dilution of both the carrier and the cryoprotectant during normal freezing and thawing.

A presently preferred vitrification solution for the prevention of cooling injury can be provided by adding polymers (e.g., antinucleating or other polymers) in concentrations that increase the tonicity of the medium to within the optimal range for inhibition of cooling injury. Anti-nucleating polymers may be selected from the group consisting of: polyglycerol, polyvinyl alcohol-polyvinyl acetate copolymer, and mixtures thereof. Other polymers contemplated for use herein include polyvinyl pyrrolidone or polyethylene glycol. Preferably, the polyethylene glycol has a mean molecular mass of 1000 daltons. Preferably the vitrification solution includes dimethyl sulfoxide, formamide, and ethylene glycol. In another preferred embodiment, the vitrification solution includes dimethyl sulfoxide, formamide, ethylene glycol, polyglycerol, and polyvinyl alcohol-polyvinyl acetate copolymer, wherein the combination of polyglycerol and polyvinyl alcohol-polyvinyl acetate copolymer is at a total concentration of 0.1 to 0.7 times isotonic. Optionally, the vitrification solution can include acetol.

The following examples illustrate various means of practicing the method of the present invention.

Example 1

Tolerability of Enormous Tonicity in the Presence of Large Concentrations of Cryoprotectant and Tolerability of Enormous Positive and Negative Step Changes in Tonicity Coupled with Large Changes in Cryoprotectant Concentration FIG. 1 shows the effects of simulating the freezing of 0.5 mm-thick rabbit renal cortical slices in either 10% w/v DMSO or 10% w/v Veg (Veg is a mixture of DMSO, formamide, and ethylene glycol in proportions disclosed below and explained in U.S. patent application Ser. No. 09/400,793 filed Sep. 21, 1999, herein incorporated by reference). In this figure and all others, the "viabilities" of the slices are indicated by the tissue K/Na ratios. The K/Na ratio is in all cases measured after restoration of physiological conditions in vitro for 90 minutes using standard and published methods.

The upper two groups of bars show the effects of exposure to 10% DMSO or to 10% Veg only. These concentrations are innocuous, and viability is 100% of that of fresh tissue slices. The data for 10% cryoprotectant (DMSO or Veg) represent what slices would experience at the time freezing begins.

The next group of bars from the top of the figure is another control, showing the effects of exposing slices to 20% w/v Veg only with no simulated freezing. Again, the K/Na ratios are in the range expected for fresh, untreated tissue.

The key results are the remaining three groups of bars, labeled "20%/40%", "to 40% D", and "to 40% V". In the first of these groups, "20%/40%", the simulation assumed that slices were frozen in 20% Veg until the total concentration of Veg reached 40%, or, in other words, until the liquid volume of the solution had been reduced to one half the initial volume. In such a situation, the vehicle solution, RPS-2 (minus calcium and magnesium) would also be concentrated by a factor of two. After exposure to this solution, slices were transferred from 40% Veg in 2X RPS-2 to 20% Veg in 1X RPS-2. Remarkably, this group demonstrated essentially no toxicity despite exposure to a vehicle solution concentrated by a factor of two at 0° C. (all exposures done at 0° C.).

In the next group, "to 40% D", the simulation was of freezing in 10% DMSO to a total concentration of 40% DMSO, which means that, in this case, the RPS-2 vehicle was also concentrated four fold. In this experiment, slices exposed to 40% DMSO were diluted, after this exposure, back to the initial reference solution in one step, with no "osmotic buffer" such as mannitol added to offset the dilution o the cryoprotectant. In other words, the slices were transferred from 40% w/v DMSO in 4X RPS-2 to 10% DMSO in 1X RPS-2. After this initial dilution, the remaining cryoprotectant was washed out in the presence of 300 mM mannitol as an osmotic buffer, in accordance with previously published methods. This group was damaged, but this is not surprising because 40% DMSO is known to be very toxic.

The final group labeled "to 40% V" is most remarkable. In this group, the simulation was of freezing in 10% Veg to a total concentration of 40% Veg, which means that, again, the RPS-2 vehicle was also concentrated four fold. Slices were then transferred from 40% Veg in 4X RPS-2 to 10% Veg in 1X RPS-2 in one step, and the 10% Veg was washed out gradually with 300 mM mannitol as an osmotic buffer. Amazingly, this group showed no demonstrable toxicity attributed to either the Veg itself or the concentrated vehicle or the abrupt 4-fold reduction in concentration in both the Veg and the RPS-2 upon dilution from 40% Veg and 4X RPS-2 to 10% Veg and 1X RPS-2 in a single step. Thus, simulated freezing and thawing is an acceptable way of rapidly adding and rapidly removing large concentrations of cryoprotectant.

Generally, in the prior art, when it is time to remove high concentrations of cryoprotectant from a cell or tissue or organ, it is necessary to increase the tonicity of the medium by adding extra impermeable solute such as mannitol or sucrose to prevent cells from swelling due to the reduction in extracellular cryoprotectant concentration. Example 1 shows the feasibility of an opposite approach: the reduction of tonicity jointly with the reduction of cryoprotectant concentration, a novel technique.

In FIG. 1, the gray and the dark bars each refer to six replicate slices treated as separate subgroups. As is evident from inspection of the figure, both duplicate sets of slices for each treatment were in close agreement, validating the overall average results for each group, which are provided by the white bars.

In Example 2, concentrations of cryoprotectant that can vitrify due to the incorporation of a 2X vehicle solution were determined to have acceptable toxicity and to profoundly suppress chilling injury.

Example 2

Cryproctectant that Vitrify in a 2X Vehicle Solution

Past published literature has indicated the chilling injury in kidney is probably due to cell shrinkage caused by incomplete penetration of cryoprotective agents into renal cells. Therefore, exposing slices to a vitrification solution containing a 2X vehicle solution prior to abrupt cooling to −20° C. was expected to lead to worse chilling injury than cooling slices to the same temperature in the same way but in the presence of a 1X vehicle solution. In fact, the exact opposite was observed. The results are given in FIGS. 2 and Table 1.

Figure 2:
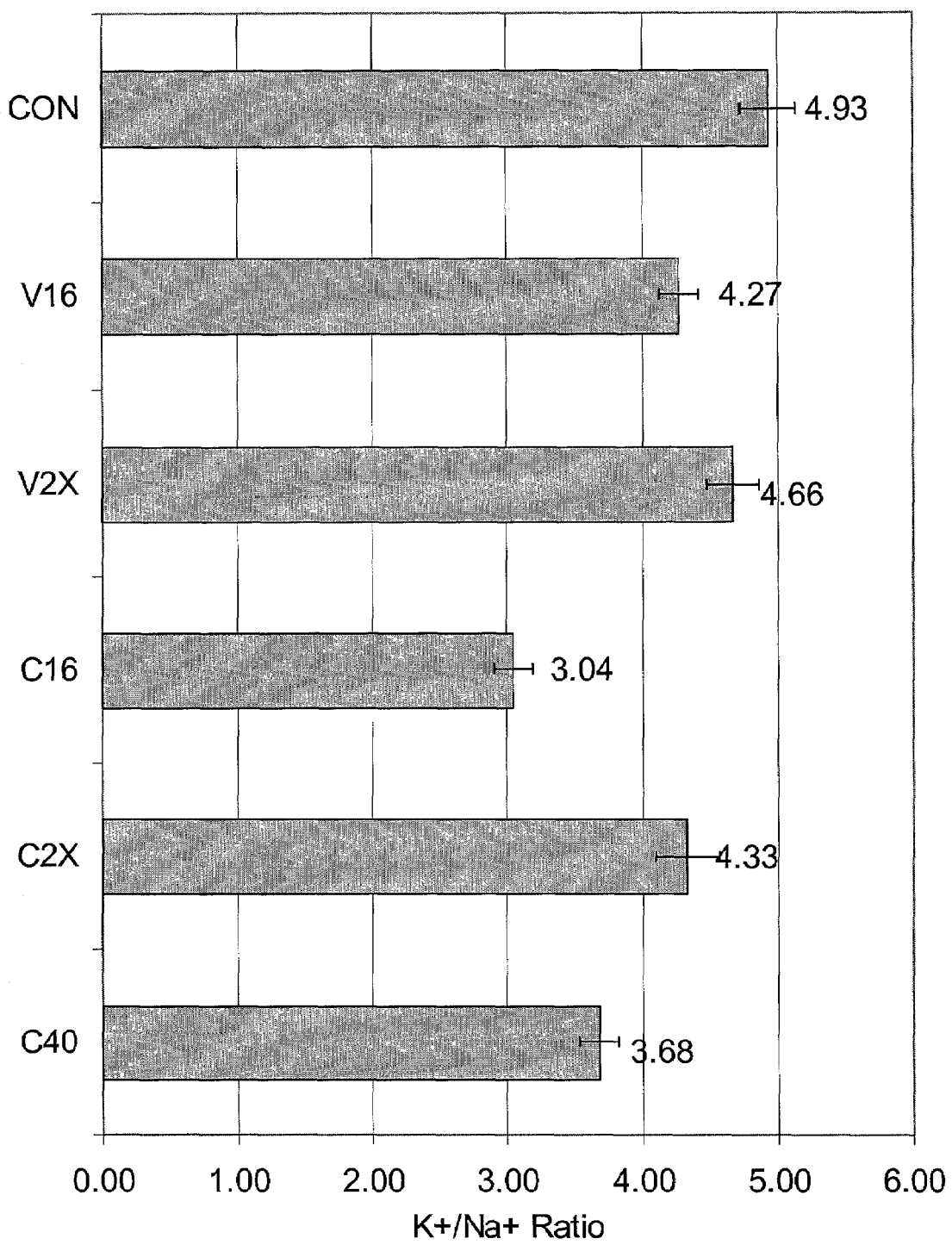
FIG. 2 shows the K/Na ratios of slices exposed to vitrifiable concentrations of cryoprotectant with or without freeze-simulation, and cooled with or without prior use of the freeze simulation method for adding cryoprotectant (simultaneous elevation of carrier solution and cryoprotectant concentration). Two vitrification solutions, V16 and C40 were used, and the effects of all treatments were compared to vehicle solution exposure only (Con). Each bar represents 12 different slices.

In FIG. 2, slices were exposed to two vitrification solutions or to vehicle solution only, as follows: "Con" refers to controls exposed only to RPS-2 at 0° C. V16 refers to exposure for 20 min at 0° C. to a vitrification solution known as "V16", a solution which is advantageous in view of its very high stability against freezing on cooling and on warming and in view of its low toxicity. V16 is the same as 55% w/v Veg solutes in 1X RPS-2, except that 2% DMSO is added to the formula. V16 was added in steps of $1/16^{th}$, $1/8^{th}$, $1/4^{th}$, $1/2$ and full-strength, then diluted, in the presence of 300 mM mannitol throughout, to $1/2$, $3/8$ths, $1/4_{th}$, $1/8^{th}$, $1/16^{th}$, and 0% of full-strength, then returned to 1X RPS-2 without mannitol. The concentration of RPS-2 was 1X throughout the procedure. Each step was 20 min in duration.

"V2X" refers to exposure to a solution containing 52% w/v Veg solutes (DMSO, formamide, and ethylene glycol, in the standard proportions) in a 2X RPS-2 vehicle solution, and, as usual, at 0° C. for 20 min. This solution was introduced by first introducing, in a series of standard steps (typically, $1/16^{th}$, $1/8^{th}$, $1/4^{th}$, and $1/2$, of the final full-strength concentration of permeating cryoprotectant), half of the full strength concentration of cryoprotectant, and by then transferring slices into the full strength solution containing 2X RPS-2 (less Ca and Mg). The slices were diluted to $1/2$ of full strength and to 1X RPS-2 in a subsequent step, 300 mM mannitol was then introduced for further dilution of the cryoprotectant. All steps were 20 min in duration. Group "C16" is a group that was cooled abruptly to −20° C. by transferring slices from V16 at 0° C. (after 20 min at that temperature) to V16 at −20° C., and subsequent holding at −20° C. for 20 min.

The group "C2X" was treated in an identical fashion except the cryoprotectant solution was the "V2X" solution instead of the "V16" solution. Finally, the last group involved a hybrid experiment between the best method known in the prior art for avoiding chilling injury and the current use of a hypertonic (greater than 1X) vehicle solution. In this group, slices were exposed to only 40% Veg at 0° C. for 20 min, in 1X RPS-2, and were then transferred to the V2X solution precooled to −20° C. and held for 20 min at that temperature as in the other chilled groups.

TABLE 1

| Treatment Group | Tonicity | K/Na | SEM | % of Control K/Na |
|---|---|---|---|---|
| Controls (1X RPS-2) | 1X | 4.93 | .21 | 100 |
| V16 (Veg* in 1X RPS-2 + 2% w/v DMSO) | 1X | 4.27 | .14 | 86.6 |
| V2X (Veg reduced by 3% W/v, in 2X RPS-2) | 2X | 4.66 | .19 | 94.6 |
| C16 (V16 cooled to −20° C.) | 1X | 3.04 | .15 | 61.7 |
| C2X (V2X cooled to −20° C.) | 2X | 4.33 | .23 | 87.9 |
| C40 (40% w/v Veg CPAs At 0° C. then transfer To V2X at −20° C.) | 1X 2X | 3.68 | .14 | 74.6 |

*Veg = 16.84% w/v ethylene glycol plus 13.96% w/v formamide plus 24.2% w/v DMSO (total concentration = 55.00% w/v); V2X contains the same solutes reduced by a factor of 52/55 ths; 40% w/v Veg CPAs consists of the same solutes reduced by a factor of 40/55 ths.

The results as indicated in FIGS. 2, are extraordinary. First, as noted above, the V16 group did very well, giving an average K/Na ratio of 4.22 against the control ratio of 4.83, which represents recovery of 87% of control viability (see tabular documentation as well). However, the V2X group did even better, reaching 96% of control viability (third bar from the bottom, K/Na=4.64). Cooling slices in V16 to −20° C. led to the expected drop in viability (K/Na of 3.05, representing just 63% of control viability). But cooling slices in V2X to −20° C. yielded a K/Na ration of 4.34, or 89.9% of control viability. Finally, using prior art technology for circumventing chilling injury, namely, cooling slices in a lower concentration of cryoprotectant to avoid cell shrinkage mediated chilling injury, but cooling them by immersing them in V2X, which is hypertonic (over 1X vehicle solution concentration), resulted in a K/Na about halfway between the results of cooling in 1X vehicle (the C16 group) and the results of cooling in 2X vehicle (the C2X group). Therefore, it was detrimental to cool from 40%, 1X as compared to cooling from 52%, 2X, in total contradiction to the prior art. Furthermore, it was more beneficial to cool into a 2X solution even starting from the initial 40%, 1X solution, as opposed to cooling into a 1X solution, again in contradiction to the prior art. These data form the initial experimental basis for the use of hypertonic solutions to reduce or eliminate chilling injury.

Example 3

The surprising results shown in Table 1 were confirmed and extended by assessing the threshold level of hypertonicity necessary for suppression of cooling injury. As shown in Table 2, the threshold for protection is astonishingly low, and appears to be near 1.2X.

TABLE 2

| Cryoprotectant* & Temperature | Tonicity | K/Na | SEM | % of Controls |
|---|---|---|---|---|
| None (1X LM5 carrier), 0° C. | 1.0X | 7.37 | 0.13 | 100 |
| Veg - 3% D(1)F in LM5, 0° | 1.0X | 7.48 | 0.20 | 101 |
| Veg - 3% D(1)F in 1.5X LM5, 0° | 1.5X | 7.38 | 0.23 | 100 |
| Veg - 3% D(1)F in 1X LM5, 0° C., Transferred to same at −20° C. | 1.0X | 5.37 | 0.10 | 72.9 |
| Veg - 3% D(1)F in 1.2X LM5, 0° C. Transferred to same at −20° C. | 1.2X | 6.75 | 0.15 | 91.7 |
| Veg - 3% D(1)F in 1.5X LM5, 0°, Transferred to same at −20° C. | 1.5X | 7.17 | 0.15 | 97.3 |

*Veg - 3% D(1)F = 16.84% w/v ethylene glycol plus 12.86% w/v formamide plus 22.3% w/v DMSO. This was experiment 00–024, carried out on Aug. 31, 2000. All solutions exposed for 20 min at 0° C. prior to cooling, and after cooling were held in the same solutions for an additional 20 min. 12 samples in each group, as in most experiments reported herein. All groups were loaded to half-strength cryoprotectant in isotonic LM5, then transferred to full strength cryoprotectant in the stated tonicity of LM5, and washed out using half strength cryoprotectant plus 300 mM mannitol in the first washout step. Lower concentrations than half-strength were added and removed as 1/16th, 1/8th, and 1/4th of full strength solutions, and a 3/8ths of full strength solution was used as well in the washout phase. All washout solutions contained 300 mM mannitol.

Table 3 shows that the factor that governs the response to cooling is primarily the level of hypertonicity, regardless of how this is established. In this table, the effect of raising the concentrations of all carrier solution solutes (except for $Ca^{2+}$ and $Mg^{2+}$, which are regularly omitted from solutions above 1X and in solutions containing cryoprotectants in order to avoid solubility issues) were compared to the effect of adding non-penetrating polymers to the solution. As can be seen, the results are similar between the two approaches. The tonicities of the impermeant additives of Table 3 are given in detail in Table 4.

TABLE 3

Prevention of Cooling Injury by Cryoprotective Polymers

| Cryoprotectant and Temperature* | Tonicity | K/Na | SEM | % of Control |
|---|---|---|---|---|
| Untreated controls in LM5, 0° C. | 1.0X | 7.19 | 0.14 | 100 |
| Veg - 3% D(1)F in 1X LM5, 0° | 1.0X | 6.88 | 0.16 | 96 |
| Veg - 3% D(1)F in 1.5X LM5, 0° | 1.5X | 6.58 | 0.16 | 91.5 |
| Veg - 3% D(1)F plus 0.7X polymers, at 0° C. (in 1X LM5) | 1.7X | 6.92 | 0.16 | 96.3 |
| Veg - 3% D(1)F in 1.5X LM5, transferred to same at −20° C. | 1.5X | 7.31 | 0.21 | 102 |
| Veg - 3% D(1)F in 1X LM5 plus 0.7X polymers, transferred to same at −20° C. | 1.7X | 6.48 | 0.14 | 90.1 |

*Veg - 3% D(1)F = 16.84% w/v ethylene glycol plus 12.86% w/v formamide plus 22.3% w/v DMSO. 0.7X polymers are 7% w/v PVP of mean molecular weight 5,000 ("PVP 5000") plus 1% w/v X1000 (a polyvinyl alcohol product commercially available from 21st Century Medicine, 10844 Edison Court, Rancho Cucamonga, CA 91730; http://www.21CM.com), and 1% w/v decaglycerol. This was experiment 00–025. All solutions exposed for 20 min at 0° C. prior to cooling, and after cooling were held in the same solutions for an additional 20 min. Groups consist of 12 samples each. Hypertonicity was present in the full-strength cryoprotectant only, other solutions being isotonic. PVP 5000 is a particularly effective polymer for promoting vitrification, and both X1000 and decaglycerol are antinucleators useful for the promotion of vitrification.

TABLE 4

Some Useful Reference Osmolalities and Tonicities

| Solution | Osmolality | Tonicity (X) |
|---|---|---|
| LM5 | 285 +/− 3 mOsm | 1.0 |
| LM5 + 1% w/v decaglycerol | 319 mOsm | 1.12 |
| LM5 + 7% w/v PVP 5,000 | 417 mOsm | 1.46 |
| LM5 + 7% w/v PVP 5,000 + 1% w/v X1000 + 1% w/v decaglycerol | 478 mOsm | 1.68 |
| LM5 + 1% w/v X1000 + 1% w/v decaglycerol | 346 mOsm (calculated) | 1.21 (calculated) |

*The composition of LM5 is disclosed in U.S. Pat. Application No. 09/916,396, "Particularly Advantageous Cryoprotectant and Carrier Solution Compositions", Fahy et al., filed Jul. 26, 2001, herein incorporated by reference (from provisional application 60/221,691, filed Jul. 31, 2000, now U.S. Pat. No. 6,869,757.).

Example 5

Protection Against Cooling Injury at Temperatures Below −20° C.

The data in FIG. 2 and in Tables 2 and 3 both show a nearly 30% reduction in K/Na ratio by cooling, relative to what was obtained with the same 1X cryoprotectant solution at 0° C. This is quantitatively the same as the drop reported before in rabbit renal cortex for a different cryoprotectant solution (for example, in Fahy et al., in Cell Biology of Trauma, J. J. Lemasters and C. Oliver, Eds, CRC Press, 1995, pp. 333-356) and is in agreement with many unpublished observations. In addition, it is known that cooling injury becomes even more severe at temperatures below −20° C. Therefore, in further experiments, lack of damage at temperatures where damage is expected is taken as evidence for successful counteraction of cooling injury.

Many experiments were done with the final solution listed in Table 3, which has a tonicity of 1.7X, including experiments investigating the effects of temperatures below 20° C. A summary of the results of these experiments is given in FIG. 3. Each type of symbol in FIG. 3 reflects a separate experiment done on a separate day. In most experiments on temperatures below −20° C., low temperature exposure was achieved by cooling the slices in containers rather than by transferring bare slices into precooled solutions as was done for experiments at about −20° C. This was necessitated by the solidification of these non-freezing solutions as temperatures approach the glass transition temperature. Therefore, FIG. 3 not only extends the observation of hypertonic suppression of cooling injury to lower temperatures, but it also extends the observation to moderate cooling rates (about 2-20° C./min).

While a tonicity of 1.7X is able to largely suppress cooling injury at −20° C., it fails to suppress cooling injury at lower temperatures. Injury continues to increase until the temperature reaches around −70° C. to −90° C., and does not increase further at lower temperatures. Despite the failure to suppress all injury, the viability retained at −135° C., which is below the glass transition temperature of the solution, is similar to the viability recorded at −20° C. for solutions cooled at a tonicity of 1X (represented by the dashed line at 68% recovery, which is 71% of the starting value of ~96% at 0° C., which reflects the levels reported in Tables 1 and 2).

The ability to postpone injury normally seen at −20° C. to below the glass transition temperature is a remarkable advance.

Figure 3:
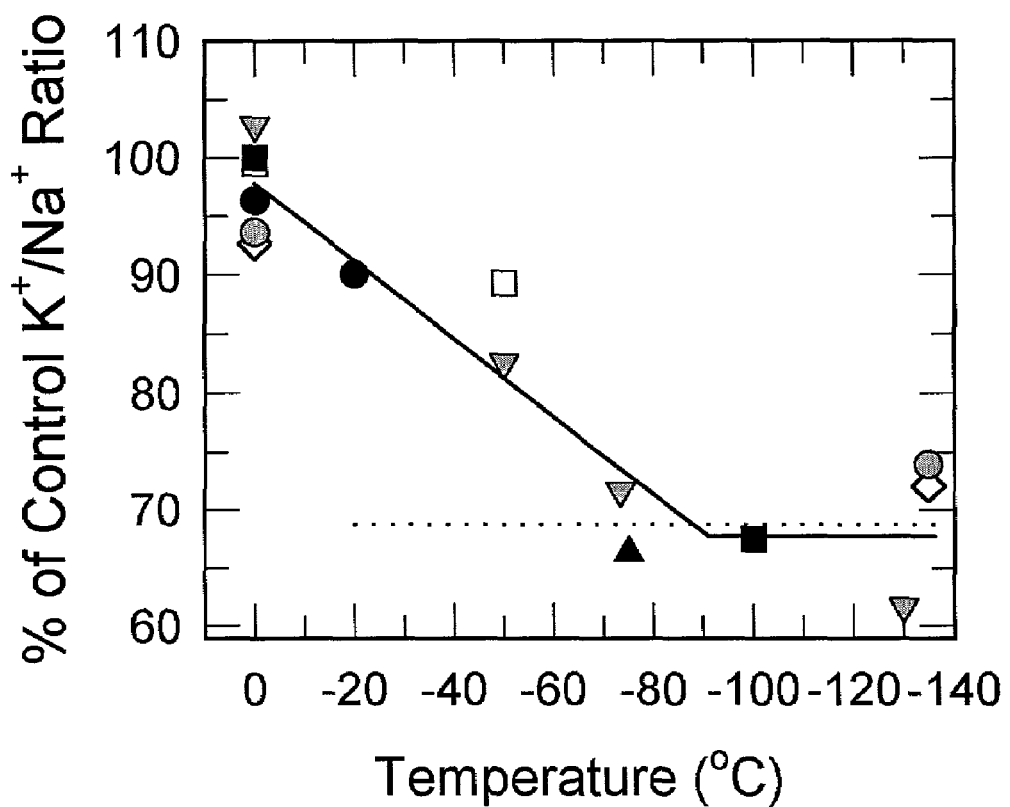
FIG. 3 shows cooling-associated damage in slices in a vitrification solution having a tonicity of 1.7X. The dotted line shows the level of damage caused in a 1X solution at about −20° C.

FIG. 3 also indicates indirectly that cooling injury is biochemical and is not an artifact of ice formation. (Ice nucleation has a zero probability above the melting point of the cryoprotectant solution, which is close to −40° C., and increases only near the glass transition temperature, or below −100° C., a pattern which is the opposite of the pattern of cooling injury.) The lack of association of injury with ice formation is evidence that the results are not an artifact of inadequate protection of the tissue from ice formation, but instead represent a real biological effect and demonstrate real attenuation thereof.

Furthermore, since these conclusions pertain even to tissues that have been vitrified (the estimated glass transition temperature for this solution is about −123° C.), it is apparent from FIG. 3 that all injury caused by vitrification and rewarming is attributable to the combination of cooling injury and cryoprotectant toxicity, both of which are addressed by the present invention. This puts the significance of the present invention into clear perspective.

Example 6

Optimum Tonicity Range for Suppressing High Temperature Cooling Injury

FIG. 3 implies that 1.7X is not the optimum tonicity for suppressing cooling injury, because cooling injury is already apparent at −20° C., in contrast to the effects reported for 1.5X solutions in Tables 2 and 3. Therefore, it was useful to define the optimal tonicity range for both high temperature and low temperature cooling injury protection.

Figure 4:
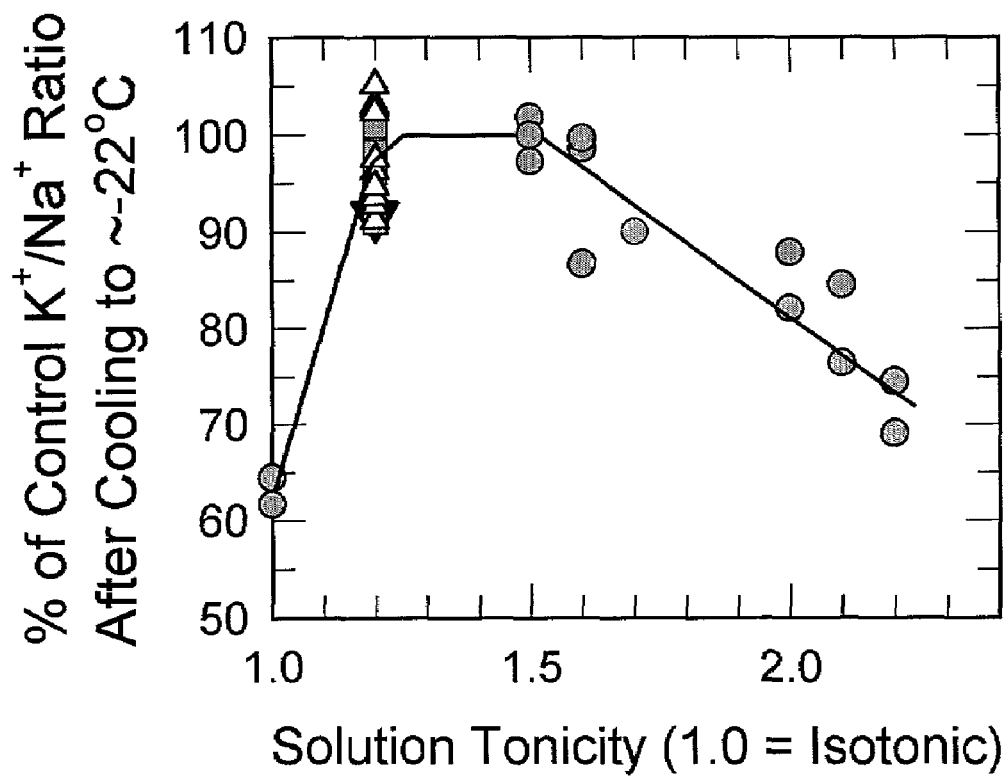
FIG. 4 shows the tonicity optimum for reducing injury caused by cooling to −22° C.

FIG. 4 shows a collection of data from many experiments in which many different cryoprotectant solutions were cooled from 0° C. to about −22° C. at different tonicities. Each symbol represents the mean of 12 rabbit renal cortical slices. For simplicity, error bars, which are typically about +/−5%, are omitted.

Based on these experiments, it appears that the optimal tonicity for protection is from around 1.2 times isotonic to around 1.5 times isotonic. Net protection is visible out to tonicities of 2.2X, but this tonicity appears to be near the outer limit of utility. Several solutions in the range of 2-2.2X were excluded due to low K/Na ratios prior to cooling (0° C. exposure yielding K/Na ratios below 90% of control); it may be that higher tonicities can have detrimental effects when background levels of cryoprotectants are high enough to be vitrifiable. In any case, it appears that the best tonicities for use at higher temperatures are from 1.2 to 1.5X.

In FIG. 3, the large black triangle plotted at 1.2X represents tonicity elevation by increased carrier solution concentration. The squares at 1.2X reflect experiments in which tonicity was elevated by the inclusion of 2% w/v polymer (decaglycerol+X1000, 1% of each). The white triangles correspond to experiments in which tonicity was elevated by 2% w/v polymer addition at 0° C. in one concentration of cryoprotectant, and the slices were thereafter transferred to more concentrated cryoprotectant solutions at the same 1.2X tonicity at −22° C. Contrary to the last experiment of Table 1, in which slices were also transferred to a higher concentration of cryoprotectant at a lower temperature but starting at 1X, the white triangles document that full protection was retained when the tonicity of the non-permeating components was effective before cooling and was kept constant during the change in cryoprotectant concentration. In all other cases shown in the figure, both the tonicity and the cryoprotectant concentration were held constant from 0° C. to −22° C.

Example 7

Figure 5:
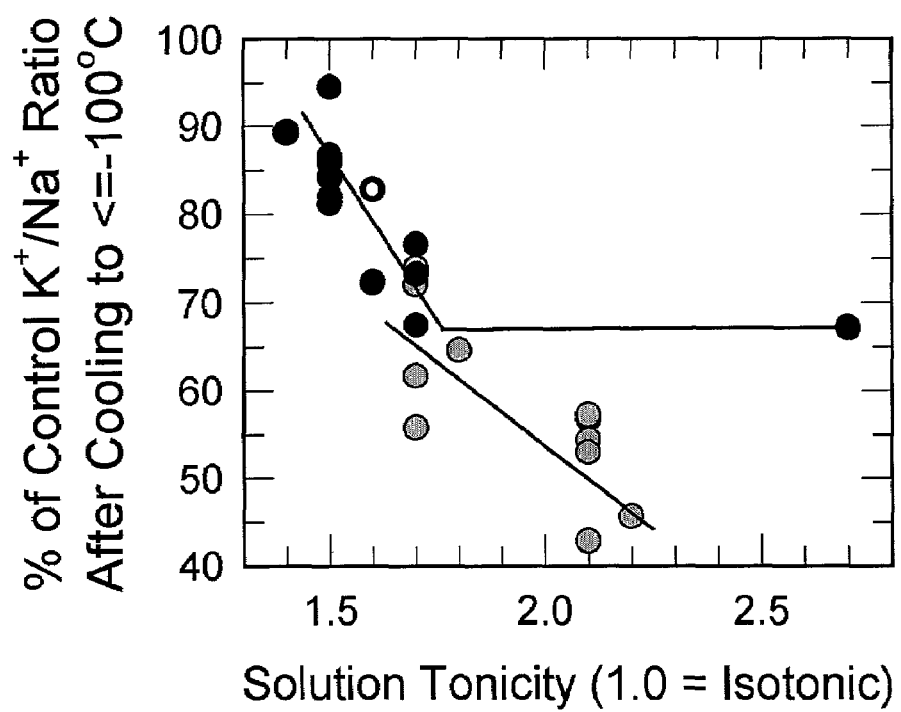
FIG. 5 shows effects of two kinds of hypertonic treatments on injury caused by cooling to −100° C. or below.

Optimum Tonicities for Suppressing Slow Cooling Injury at Temperatures of −100° C. and Below, and Effective Methods Involving Two Stages of Hypertonic Exposure for the Optimization of Cooling Injury Suppression The results presented above indicate that the tonicity optimum is rather narrow at both high and low temperatures. FIG. 5 provides more information about the locus of the optimum and about a strategy for broadening the optimum.

FIG. 5 shows the results of two kinds of experiments: First, FIG. 5 shows the results of cooling solutions having tonicities of 1.7, 1.8, 2.1, and 2.2 times isotonic (gray circles). There is a clear downward trend as tonicity rises, suggesting that tonicities below 1.7 will yield better results than the already very good results presented in FIG. 3.

Second, results are reported for many experiments (white and black points) in which one tonicity was used for cooling to about −22° C., and then the tonicity was elevated prior to deeper cooling (allowing at least 20 min for the higher tonicity to be experienced by the 0.5 mm-thick tissue slices at −22° C.). In one extreme case, changing from 2.0X to 2.7X at −22° C. prior to cooling to −100° C. (point plotted at 2.7X) allowed good recovery, whereas poor recovery would be predicted using a protocol in which 2.7X is present at all temperatures from 0° C. through −100° C., based on the gray points shown in the figure.

In a more moderate case, samples cooled to −22° C. in tonicities ranging from 1.2X to 2X (1.2X to 1.5X in all but one case) and then switched to 1.7X prior to further cooling (black points plotted at 1.7X) did on average better than samples that were cooled in 1.7X from zero degrees all the way to the final temperatures (gray points at 1.7X). This strategy may be useful for vitrification solutions that may require higher tonicities than are optimal for the inhibition of cooling injury, as some of the detrimental effect of these supraoptimal tonicities may be negated by using lower tonicities at higher temperatures prior to jumping to the final tonicity required.

In any case, the use of the two-step tonicity approach (wherein the first tonicity was 1.2X) yielded recoveries consistently over 70% for 1.6X and 80% for 1.5X, with a single recovery of nearly 90% for 1.4X, and with one recovery of 95% for a solution whose final tonicity was 1.5X. In the latter case, the final temperature was −130° C., and the solution used for cooling to this temperature was Veg-3% D(1)F+7% acetol+1% X1000+4% decaglycerol in an LM5 carrier solution. These results compare favorably to the ~25-30% recovery obtainable after vitrifying in VS41A and the ~50-60% recovery obtainable with the solutions described in U.S. patent application Ser. No. 09/400,793, filed Sep. 21, 1999, "Improved Cryoprotectant Solutions" application (herein incorporated by reference).

Based on the data in FIGS. 3, 4, and 5, it was apparent that a good tonicity for cooling to about −22° C. might be in the middle of the range between 1.2X and 1.5X. Consequently, the following experiment was performed. In the description of the experiment below, all percentages are percent weight/volume (% w/v, or grams per deciliter).

Group Treatment
1 Controls (LM5 carrier solution only)
2 Expose to the following solution for 20 min at 0° C.:
  Veg-3% D(1)F, plus
  1% X1000 plus 2.5% decaglycerol (1.35X tonicity)
  3 Expose to the same solution as in group 2 in the same way, but then transfer to a −22° C. solution containing the above ingredients but containing as well 7% acetol and an additional 1.5% decaglycerol, and hold in that solution for 30 minutes for equilibration (1.35X jumps to 1.5X).
4 Same as group 3, but use 7% ethylene glycol in place of 7% acetol
5 Same as group 3, but cool to −110° C.

The solution used in groups 3 and 5 is virtually stable on warming at a rate of 5° C./minute (only 0.2% of the solution mass is able to crystallize at this warming rate). The solution used in groups 4 and 6 is stable on warming at a rate of 2.9° C./min, based on the same criterion. Consequently, these solutions are applicable to large systems such as organs and engineered tissues.

The results of the above experiment are as follows:

TABLE 5

| Group | K/Na | % of Control | SEM in % of Control |
|---|---|---|---|
| 1 | 5.60 | 100 | 2.23 |
| 2 | 5.86 | 104.6 | 2.51 |
| 3 | 4.87 | 86.9 | 2.20 |
| 4 | 5.34 | 95.3 | 1.25 |
| 5 | 4.89 | 87.3 | 1.93 |

The results of Table 5 indicate that a 1.35X solution is innocuous at 0° C., and that cooling from it into two vitrification solutions yielded high recovery from −22° C., in one case reacing 95%. Further cooling in the 1.5X solution to −110° C. produced no injury beyond what was observed at −22° C. for the first vitrification solution. Another variation on this experiment, in which tonicity is maintained at 1.35X at both high and lower temperatures, is being conducted and is expected to yield good results.

SUMMARY

These examples indicate that, unlike the prior art, the hypertonicity approach can eliminate up to 95% of all damage associated with exposing living tissues to vitrifiable concentrations, cooling them to below the glass transition temperature, rewarming them, and removing the cryoprotectant, and that the technique pertains to both rapid and slow cooling protocols. The present invention therefore brings the prospect of cryopreservation of large and delicate structures, such as organs and engineered tissues, dramatically closer to practical realization.

In addition, optimum protocols for two-step tonicity change have not been precisely defined, but such fine-tuning is enabled based on the current disclosure. Furthermore, the examples presented herein may not precisely define the tonicity optimum for all living systems. However, the hypertonicity method may be practiced for all living systems based on the present disclosure, because the optimum range of tonicity can be found for any living system based on the examples provided herein of the ability to identify such a range for one system. Similarly, the tolerable osmotic limits for various living systems may vary, but all systems can be submitted to the freeze simulation protocol to determine what the limits are for specific systems. Osmotic limits for many cells are widely known. Furthermore, for combating cooling injury, it is anticipated that, in the examples here, the most desirable level of hypertonicity will generally be lower than the upper osmotic limit of the system.

Other variations of the preferred embodiments will be apparent to one of skill in the art with reference to the following claims.

What is claimed is:

1. A method for minimizing or eliminating injury to a living system selected from the group consisting of animal cells and animal tissue; caused by cooling said living system without the formation of ice therein, said method comprising:
  adding to said living system a preservation medium having a tonicity which is sufficiently hypertonic to minimize injury caused by said cooling, wherein said preservation medium has a tonicity between 1 and 4 times isotonic, and wherein said preservation medium comprises a carrier solution and at least one cryoprotective agent which is sufficient in concentration to prevent freezing at a predetermined temperature below approximately 0° C.; and
  cooling the living system to said predetermined temperature, thereby minimizing or eliminating injury caused by said cooling.

2. The method of claim 1, wherein the tonicity is from 1.1 to 2.7 times isotonic.

3. The method of claim 1, wherein the tonicity is from 1.1 to 2 times isotonic.

4. The method of claim 1, wherein the tonicity is from 1.1 to 1.5 times isotonic.

5. The method of claim 1, wherein the tonicity is from 1.2 to 1.5 times isotonic.

6. The method of claim 1, wherein the tonicity of the preservation medium is increased by increasing the concentration of said carrier solution.

7. The method of claim 6, wherein the tonicity of the carrier solution is raised simultaneously with an increase in concentration of said cryoprotective agent.

8. The method of claim 7, wherein the tonicity of the carrier solution is increased by a proportion which is approximately equal to the proportional increase in the concentration of said cryoprotective agent.

9. The method of claim 1, wherein said at least one cryoprotective agent comprises dimethyl sulfoxide, formamide, and ethylene glycol, and optionally further comprises acetol.

10. The method of claim 9, wherein said at least one cryoprotective agent further comprises polyglycerol and polyvinyl alcohol-polyvinyl acetate copolymer, and wherein the combination of polyglycerol and polyvinyl alcohol-polyvinyl acetate copolymer is at a total concentration of 0.1 to 0.7 times isotonic.

11. A method for minimizing or eliminating injury to a living system selected from the group consisting of animal cells and animal tissue; caused by cooling said living system without the formation of ice therein, said method comprising:
  adding to said living system a preservation medium having a tonicity which is sufficiently hypertonic to minimize injury caused by said cooling, wherein said preservation medium has a tonicity between 1 and 4 times isotonic, and wherein said preservation medium comprises a carrier solution, at least one cryoprotective agent, and at least one polymer, wherein said cryoprotective agent and said polymer are sufficient in concentration to prevent freezing at a predetermined temperature below approximately 0° C.; and cooling the living system to said predetermined temperature, thereby minimizing or eliminating injury caused by said cooling.

12. The method of claim 11, wherein the at least one polymer is selected from the group consisting of polyglycerol, polyvinyl alcohol-polyvinyl acetate copolymer, polyvinyl pyrrolidone, polyethylene glycol, and mixtures thereof.

13. The method of claim 12 wherein said polyethylene glycol has a mean molecular mass of approximately 1000 daltons.

14. A method for minimizing or eliminating injury to a living system selected from the group consisting of animal cells and animal tissue, caused by cooling said living system without the formation of ice therein, said method comprising:

contacting said living system with a first protective solution prepared by adjusting the hypertonicity of the solution to be within a first tonicity range for minimizing injury caused by said cooling within a first predetermined temperature range, wherein said first protective solution has a tonicity between 1 and 4 times isotonic;

cooling the living system to a temperature within said first temperature range below approximately 0° C., contacting said living system with a second protective solution prepared by adjusting the hypertonicity of the solution to be within a second tonicity range for minimizing injury caused by said cooling within a second predetermined temperature range below approximately 0° C.; wherein said second protective solution has a tonicity between 1 and 4 times isotonic; and cooling the living system to a temperature within said second temperature range, thereby minimizing or eliminating injury caused by said cooling.

15. The method of claim 14, wherein said first protective solution has a hypertonicity lower than the hypertonicity of said second protective solution.

16. The method of claim 14, wherein said first protective solution contains at least one antinucleating polymer.

17. The method of claim 14, wherein said second protective solution contains at least one antinucleating polymer.

18. The method of claim 14, wherein said first protective solution contains polyvinyl pyrrolidone.

19. The method of claim 14, wherein said second protective solution contains polyvinyl pyrrolidone.

20. The method of claim 14, wherein said first protective solution contains polyethylene glycol having a mean molecular mass of approximately 1000 daltons.

21. The method of claim 14, wherein said second protective solution contains polyethylene glycol having a mean molecular mass of approximately 1000 daltons.

* * * * *